United States Patent
Edsberg et al.

(10) Patent No.: US 12,178,810 B2
(45) Date of Patent: Dec. 31, 2024

(54) TESOFENSINE AND METOPROLOL FOR TREATMENT OF HYPERTENSION

(71) Applicant: SANIONA A/S, Glostrup (DK)

(72) Inventors: Berit Edsberg, Kongens Lyngby (DK); Thomas Amos Jacobsen, Ølsted (DE)

(73) Assignee: Saniona A/S, Glostrup (DK)

( * ) Notice: Subject to any disclaimer, the term of this patent is extended or adjusted under 35 U.S.C. 154(b) by 957 days.

(21) Appl. No.: 17/116,849

(22) Filed: Dec. 9, 2020

(65) Prior Publication Data

US 2021/0093628 A1    Apr. 1, 2021

Related U.S. Application Data

(63) Continuation of application No. 16/068,255, filed as application No. PCT/DK2016/050477 on Dec. 30, 2016, now abandoned.

(30) Foreign Application Priority Data

Jan. 15, 2016    (DK) ............................ PA 2016 70018

(51) Int. Cl.
  *A61K 31/46*    (2006.01)
  *A61K 31/138*   (2006.01)
  *A61P 9/12*     (2006.01)

(52) U.S. Cl.
  CPC ............ *A61K 31/46* (2013.01); *A61K 31/138* (2013.01); *A61P 9/12* (2018.01)

(58) Field of Classification Search
  CPC .......... A61K 31/46; A61K 31/138; A61P 9/12
  USPC ....................................................... 514/304
  See application file for complete search history.

(56) References Cited

U.S. PATENT DOCUMENTS

| | | | |
|---|---|---|---|
| 9,211,271 B2 | 12/2015 | Hansen et al. | |
| 9,387,184 B2 | 7/2016 | Hansen et al. | |
| 9,579,288 B2 | 2/2017 | Nielsen et al. | |
| 10,537,551 B2 | 1/2020 | Nielsen et al. | |
| 2010/0056758 A1 | 3/2010 | Deveaux et al. | |
| 2016/0279067 A1* | 9/2016 | Nielsen ................. | A61K 45/06 |

FOREIGN PATENT DOCUMENTS

| WO | 97/30997 A1 | 8/1997 |
|---|---|---|
| WO | 2004/110368 A2 | 12/2004 |
| WO | 2007/030997 A1 | 3/2007 |
| WO | 2013/120935 A1 | 8/2013 |
| WO | 2016/138908 A1 | 9/2016 |

OTHER PUBLICATIONS

"The Fourth Report on the Diagnosis, Evaluation, and Treatment of High Blood Pressure in Children and Adolescents", Pediatrics, Aug. 2004, vol. 114, No. 2, 555-576.
Astrup A, Madsbad S, Breum L, Jensen T, Kroustrup J and Meinert T, "Effect of tesofensine on bodyweight loss, body composition, and quality of life in obese patients: a randomised, double-blind, placebo-controlled trial", Lancet, Nov. 2008, 372(9653):1906-13.
Bentzen et al., "Anti-hypertensive treatment preserves appetite suppression while preventing cardiovascular adverse effects of tesofensine in rats", Obesity, May 2013, vol. 21, No. 5, 985-992.
Hamadeh et al., Impact of CYP2D6 Polymorphisms on Clinical Efficacy and Tolerability of Metoprolol Tartrate, Clinical pharmacology & Therapeutics I vol. 96 No. 2 I Aug. 2014 (Year: 2014).
Kostis, John B. et al., "Central nervous system effects of /3-adrenergic blocking drugs: the role of ancillary properties", Circulation 75(1), 204-212, 1987.
LaPalio et al., Safety And E^^cacy of Metoprolol in the Treatment of Hypertension in the Elderly, Journal of the American Geriatrics Society / vol. 40, Issue 4, 1992 (Year: 1992).
Messerli, Franz H. et al., "Body Weight Changes with B-Blocker Use: Results from GEMINI", The American Journal of Medicine, vol. 120, 610-615, 2007.
Sarafidis et al., Comparative Efficacy of Two Different b-Blockers on 24-Hour Blood Pressure Control, The Journal of Clinical Hypertension, vol. 10 No. Feb. 2, 2008 (Year: 2008).
Angulo et al., "Prader-Willi syndrome: A review of clinical, genetic, and endocrine findings", J. Endocrinol. Invest., 2015, 38, 1249-1263.
Aycan et al., "Prader-Willi Syndrome and Growth Hormone Deficiency", J. Clin. Res. Pediatr. Endocrinol., 2014, 6(2), 62-67.
Cassidy et al., "Prader-Willi Syndrome", Genetics in Medicine, 2012, 14(1), 10-26.
Irizarry et al., "Prader Willi Syndrome: Genetics, Metabolomics, Hormonal Function, and New Approaches to Therapy", Adv. Pediatr., Aug. 2016, 63(1), 47-77.
Wattendorf et al., "Prader-Willi Syndrome", American Family Physician, Sep. 1, 2005, vol. 72, No. 5, 827-830.

* cited by examiner

*Primary Examiner* — Kristin A Vajda
(74) *Attorney, Agent, or Firm* — BakerHostetler

(57) ABSTRACT

The present invention relates to treatment of hypertension using a combination of tesofensine and metoprolol. The treatment is particularly well suited for the treatment of hypertensive obese subjects and hypertensive diabetic subjects.

12 Claims, 3 Drawing Sheets

TESOFENSINE AND METOPROLOL FOR TREATMENT OF HYPERTENSION

CROSS REFERENCE TO RELATED APPLICATIONS

This application is a continuation of U.S. application Ser. No. 16/068,255, filed Jul. 5, 2018, which is the national stage of International Application No. PCT/DK2016/050477, filed Dec. 30, 2016, which claims the benefit of Denmark Application No. PA 2016 70018, filed Jan. 15, 2016, the entireties of which are incorporated by reference herein.

FIELD OF INVENTION

The present invention relates to the treatment of hypertension using a combination of tesofensine and metoprolol, particularly to the treatment of hypertensive obese subjects and hypertensive diabetic subjects.

BACKGROUND OF INVENTION

Hypertension, i.e. high blood pressure, is a chronic medical condition in which the blood pressure in the arteries is persistently elevated. Sustained hypertension over time is a major risk factor for hypertensive heart disease, coronary artery disease, stroke, aortic aneurysm, peripheral artery disease, and chronic kidney disease. Worldwide, high blood pressure is estimated to cause 7.5 million deaths, about 12.8% of the total of all deaths.

Within the past decades the prevalence of obesity has also risen in virtually all ethnic, racial and socioeconomic populations, in both genders and in all age groups. Obesity is associated with a significantly elevated risk for type 2 diabetes, coronary heart diseases, hypertension and numerous other major illnesses and overall mortality from all causes. Therefore, weight reduction and reduction of blood pressure is usually critical for the obese patient.

Control of hypertension is also a major focus area in the treatment of diabetic subjects since most people with diabetes develop high blood pressure during their life. Hypertension can lead to and make worse many complications of diabetes, including diabetic eye disease and kidney disease.

Tesofensine, first described in WO 97/30997, is a triple monoamine reuptake inhibitor in clinical development for the treatment of obesity. Tesofensine effectively produces weight loss in obese individuals of about twice of that seen with currently marketed anti-obesity drugs. In general, tesofensine is well tolerated in humans, but at therapeutic relevant doses it has been found that heart rate and, at higher doses, also blood pressure increased due to a well understood mechanism of action driven effect (activation of adrenergic receptors) (Astrup et al 2008, Lancet 372:1906-13). Animal studies have shown that co-administration of tesofensine and metoprolol is capable of preventing the tesofensine-induced increase in heart rate and blood pressure without reducing the weight loss efficacy of tesofensine (WO 2013/120935 and Hjorth Bentzen et al 2013; Obesity; Vol 21(5), p. 985-992).

Metoprolol is a selective β1 (adrenergic) receptor blocker. Metoprolol has been used to treat various cardiovascular disorders including angina, arrhythmias, tachycardia, myocardial infarction, heart failure and hypertension.

The effect of metoprolol on blood pressure has previously been investigated (Kostis et al (Circulation 75(1), 204-212, 1987). Kostis et al has shown that metoprolol treatment decreases supine systolic and diastolic blood pressure by about 4 mmHg in healthy male subjects.

There is impetus for creating new and alternative treatments for management of hypertension and, in particular, management of hypertension in obese individuals.

SUMMARY OF INVENTION

The present inventors have surprisingly found that co-administration of tesofensine and metoprolol to human subjects results in a significant decrease in both systolic and diastolic blood pressure. The observed effect on blood pressure is higher than the effect achievable from metoprolol alone. The expectation is that Tesofensine increases blood pressure and that metoprolol may act to prevent this increase in blood pressure. Therefore it is unexpected that the combination leads to a decrease in blood pressure. The blood pressure lowering effect of co-administration of Tesofensine with Metoprolol has been confirmed in healthy subjects (example 2) and in subjects with Type 2 diabetes (example 3). The experimental data also confirm that the combination of Tesofensine with Metoprolol is effective in inducing weight loss and in reducing blood pressure at the same time.

Thus, the present invention relates to the use of tesofensine and metoprolol for reduction of blood pressure, i.e. in one aspect for treatment of hypertension.

In a first aspect, the present disclosure relates to a method for treatment of hypertension in a subject, the method comprising administering to said subject in need thereof:
  i) a therapeutically effective amount of tesofensine or a pharmaceutically acceptable salt thereof; and
  ii) a therapeutically effective amount of metoprolol or a pharmaceutically acceptable salt thereof, thereby reducing blood pressure in said subject.

In another aspect, the present disclosure relates to a method for reducing blood pressure in a subject, the method comprising administering to said subject in need thereof:
  i) a therapeutically effective amount of tesofensine or a pharmaceutically acceptable salt thereof; and
  ii) a therapeutically effective amount of metoprolol or a pharmaceutically acceptable salt thereof,
thereby reducing blood pressure in said subject.

The present disclosure further relates to a composition comprising
  i) a therapeutically effective amount of tesofensine or a pharmaceutically acceptable salt thereof; and
  ii) a therapeutically effective amount of metoprolol or a pharmaceutically acceptable salt thereof,
for use in the treatment of hypertension or for reduction of blood pressure.

In yet another aspect, the present disclosure relates to use of the composition as described herein in the manufacture of a medicament for the treatment of hypertension or for reduction of blood pressure.

Co-treatment with tesofensine and metoprolol is capable of reducing both weight and blood pressure in a subject. Thus, in yet another aspect, the present disclosure relates to a method for treatment of hypertension and obesity in a subject in need thereof, the method comprising administering to said subject:
  i) a therapeutically effective amount of tesofensine or a pharmaceutically acceptable salt thereof; and
  ii) a therapeutically effective amount of metoprolol or a pharmaceutically acceptable salt thereof,
thereby reducing blood pressure and body weight of said subject.

The composition comprising tesofensine and metoprolol as described herein is particularly well suited for use in the treatment of hypertensive obese and/or diabetic subjects.

DETAILED DESCRIPTION OF THE INVENTION

Figure 1:
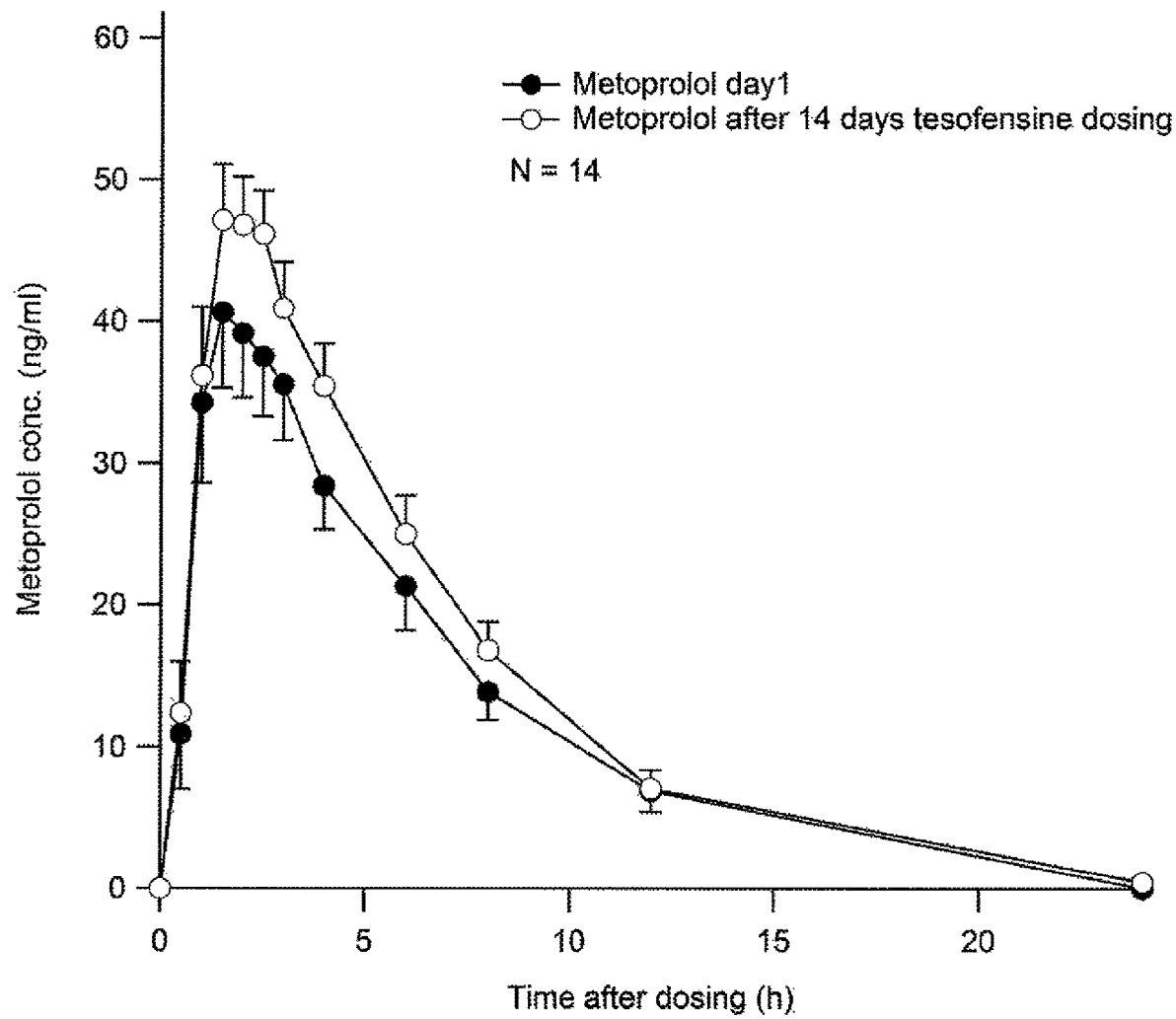
FIG. 1. PK of metoprolol after a single dosing in absence and presence of tesofensine at steady state. Single dose metoprolol pharmacokinetics (PK, 50 mg/kg) obtained at day 0 was compared to the PK obtained after 14 days of tesofensine once daily administration (2 mg loading dose at days 1-3, 0.5 mg maintenance dose at days 4-14).

The data in the present application shows that tesofensine and metoprolol co-administration efficiently reduces blood pressure, wherefore their combined use is proposed herein for the treatment of hypertension. The data also confirm that tesofensine and metoprolol co-administration effectively reduces weight and blood pressure, wherefore the combined use is proposed herein for the treatment of hypertension and obesity or an obesity related disorder as herein defined.

Tesofensine

The treatment described herein comprises administration of an active pharmaceutical ingredient (API) selected from tesofensine or a pharmaceutically acceptable salt thereof.

Tesofensine [(1R,2R,3S,5S)-3-(3,4-dichlorophenyl)-2-(ethoxymethyl)-8-methyl-8-azabicyclo[3.2.1]octane] is a centrally acting triple monoamine re-uptake inhibitor (MRI) with intrinsic inhibitory activity on noradrenaline, serotonin and dopamine transporter function. When corrected for placebo and diet effects, long-term tesofensine treatment produces a weight loss of about 10% in obese patients, which is approximately twice as much as that achieved by currently marketed anti-obesity drugs.

The chemical structure of tesofensine is

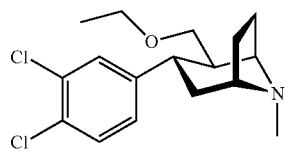

Preclinical and clinical data suggest that appetite suppression is an important mechanism by which tesofensine exerts its robust weight-reducing effect. In addition, tesofensine has also been demonstrated to increase nocturnal energy expenditure in human subjects. These findings have recently been corroborated and extended in preclinical settings, demonstrating that tesofensine induces a robust and sustained weight loss in a rat model of diet-induced obesity (DIO) of which the long-lasting reduction in body weight is caused by appetite suppression with a gradual increase in energy expenditure. Notably, the hypophagic effect of tesofensine in DIO rats is critically dependent on stimulated al adrenoceptor activity, and to a less extend dopamine D1 receptor function, indicating that enhancement of central noradrenergic and dopaminergic neurotransmission constitute important mechanisms underlying the robust appetite-suppressing effect of tesofensine.

Overall, chronic tesofensine treatment is associated with minor adverse events, and with minimal cardiovascular effects, suggesting that tesofensine may generally be a well-tolerated long-term treatment for obesity. However, dose-dependent elevations in heart rate and significant increases in blood pressure have been reported in obese individuals.

Examples of pharmaceutically acceptable salts include, without limitation, the non-toxic inorganic and organic acid addition salts such as the hydrochloride, the hydrobromide, the nitrate, the perchlorate, the phosphate, the sulphate, the formate, the acetate, the aconate, the ascorbate, the benzenesulphonate, the benzoate, the cinnamate, the citrate, the embonate, the enantate, the fumarate, the glutamate, the glycolate, the lactate, the maleate, the malonate, the mandelate, the methanesulphonate, the naphthalene-2-sulphonate, the phthalate, the salicylate, the sorbate, the stearate, the succinate, the tartrate, the toluene-p-sulphonate, and the like. Such salts may be formed by procedures well known and described in the art.

Examples of pharmaceutically acceptable cationic salts of an API include, without limitation, the sodium, the potassium, the calcium, the magnesium, the zinc, the aluminium, the lithium, the choline, the lysinium, and the ammonium salt, and the like, of an API containing an anionic group. Such cationic salts may be formed by procedures well known and described in the art.

In the context of this disclosure the "onium salts" of N-containing compounds are also contemplated as pharmaceutically acceptable salts. Preferred "onium salts" include the alkyl-onium salts, the cycloalkyl-onium salts, and the cycloalkylalkyl-onium salts.

In one embodiment of the present disclosure, tesofensine is selected from the free base, the citrate salt and the tartrate salt.

The tesofensine or pharmaceutically acceptable salt thereof is usually administered orally.

Tesofensine is normally administered at a daily dose of about 0.25-2 mg API (active pharmaceutical ingredient).

In one embodiment of the present disclosure tesofensine or pharmaceutical salt thereof is administered at about 0.25 mg or about 0.5 mg API per day, such as at about 0.2 mg to about 0.3 mg or about 0.45 to about 0.55 mg API per day.

In one embodiment of the present disclosure tesofensine or pharmaceutical salt thereof is administered in a range of from about 0.1 mg to about 4 mg API per day, such as about 0.1 mg to about 3 mg API per day, for example about 0.1 to about 2.5 mg API per day, such as about 0.1 to about 2 mg API per day, such as about 0.1 to about 1.5 mg API per day, for example about 0.1 mg to about 1 mg API per day, such as about 0.1 mg to about 0.8 mg API per day, for example about 0.1 mg to about 0.7 mg API per day, such as about 0.1 mg to about 0.6 mg API per day, for example about 0.1 mg to about 0.5 mg API per day, such as about 0.1 mg to about 0.4 mg API per day, for example about 0.1 mg to about 0.3 mg API per day, such as about 0.1 mg to about 0.2 or about 0.2 to about 0.3 mg API per day.

In one embodiment of the present disclosure tesofensine is administered in a range of from about 0.5 mg to about 4 mg API per day, such as about 1 mg to about 4 mg API per day, for example about 1.5 mg to about 4 mg API per day, such as about 2 mg to about 4 mg API per day.

In one embodiment, the tesofensine or a pharmaceutically acceptable salt thereof is administered at 0.1-1.5 mg API per day, for example 0.1-1 mg API per day, such as 0.2-0.8 mg API per day, for example 0.25-0.75 mg API per day, such as 0.4-0.6 mg API per day, for example about 0.2 mg API per day, 0.25 mg API per day, 0.5 mg API per day or 0.75 mg API per day.

In one embodiment of the present disclosure tesofensine is administered in a range of from about 0.01 mg to about 0.4 mg API per day, such as about 0.01 mg to about 0.3 mg API per day, for example about 0.01 mg to about 0.2 mg API per day, such as about 0.01 mg to about 0.1 mg API per day.

In one embodiment of the present disclosure tesofensine is administered in a range of from about 0.05 mg to about 0.4 mg API per day, such as about 0.05 mg to about 0.3 mg API per day, for example about 0.05 mg to about 0.2 mg API per day, such as about 0.05 mg to about 0.1 mg API per day.

In one embodiment of the present disclosure tesofensine is administered in a range of from about 0.05 mg to about 0.10 mg API per day, such as about 0.10 mg to about 0.15 mg API per day, for example about 0.15 mg to about 0.20 mg API per day, such as about 0.20 mg to about 0.25 mg API per day.

In one embodiment, the tesofensine or a pharmaceutically acceptable salt thereof is administered at about 0.1-0.3 mg API per day.

In one embodiment, the tesofensine or a pharmaceutically acceptable salt thereof is administered at about 0.2-0.4 mg API per day.

In one embodiment, the tesofensine or a pharmaceutically acceptable salt thereof is administered at about 0.4-0.6 mg API per day.

In one embodiment, the tesofensine or a pharmaceutically acceptable salt thereof is administered at about 0.6-0.8 mg API per day.

The daily dosage of tesofensine may be administered in one or several doses, such as two, per day. In one embodiment, the daily dosage is administered in one dose.

Metoprolol

Metoprolol, i.e. 1-(Isopropylamino)-3-[4-(2-methoxyethyl)-phenoxy]-propan-2-ol, branded under various trade names, is a selective β1 (adrenergic) receptor blocker. Metoprolol has been used to treat various cardiovascular disorders including angina, arrhythmias, tachycardia, myocardial infarction, heart failure and hypertension. The plasma T % for metoprolol is 3-4 hours.

Common side effects of metoprolol include trouble sleeping, feeling tired, feeling faint, and abdominal discomfort. Large doses may cause serious toxicity. Metoprolol has also been reported to lead to weight gain (Messerli et al, The American Journal of Medicine (2007) 120, 610-615).

Suitable pharmaceutically acceptable salts of metoprolol include any of the salts mentioned herein and preferably include the tartrate, succinate, fumarate or benzoate salts and especially the succinate salt. The S-enantiomer of metoprolol or a salt thereof, particularly the benzoate salt or the sorbate salt, may also be used.

In one embodiment of the present disclosure metoprolol or a pharmaceutically acceptable salt thereof is administered at 10-200 mg API per day, such as 25-100 mg API per day or 50-150 mg API per day, for example 80-120 mg API per day, such as 90-110 mg API per day.

In one embodiment of the present disclosure metoprolol or a pharmaceutically acceptable salt thereof is administered at 10-100 mg API per day, such as 10-80 mg API per day, for example 10-50 mg API per day, such as 10-30 mg API per day.

The metoprolol or pharmaceutically acceptable salt thereof is usually administered orally.

The daily dosage of metoprolol may be administered in one or several doses per day. In one embodiment, the daily dosage is administered in two or more doses.

In one embodiment, the metoprolol is administered as a pharmaceutical composition having an extended release profile, e.g. as disclosed in WO 2016/138908 (incorporated by reference).

Co-Administration of Tesofensine and Metoprolol

According to the present disclosure tesofensine is co-administered with metoprolol for the treatment or alleviation of hypertension in a subject in need thereof. Preferably, the treatment disclosed herein results in a reduction of blood pressure exceeding that of metoprolol treatment alone.

Thus, in one embodiment, the present disclosure relates to a method for treatment of hypertension in a subject, the method comprising administering to said subject in need thereof:
  i) a therapeutically effective amount of tesofensine or a pharmaceutically acceptable salt thereof; and
  ii) a therapeutically effective amount of metoprolol or a pharmaceutically acceptable salt thereof,
thereby reducing blood pressure in said subject.

Hypertension usually does not cause symptoms initially, but sustained hypertension over time is a major risk factor for hypertensive heart disease, coronary artery disease, stroke, aortic aneurysm, peripheral artery disease, and chronic kidney disease.

Blood pressure is expressed by two measurements, the systolic and diastolic pressures, which are the maximum and minimum pressures, respectively, in the arterial system. The systolic pressure occurs when the left ventricle is most contracted; the diastolic pressure occurs when the left ventricle is most relaxed prior to the next contraction. The blood pressure values given herein represent values at rest, e.g. supine blood pressure, unless otherwise indicated.

In people aged 18 years or older hypertension is defined as a systolic and/or a diastolic blood pressure consistently higher than an accepted normal value—see table herein below.

| Category | Systolic, mm Hg | Diastolic, mm Hg |
| --- | --- | --- |
| Normal | 90-119 | 60-79 |
| High Normal (pre-hypertension) | 120-139 | 80-89 |
| Stage 1 hypertension | 140-159 | 90-99 |
| Stage 2 hypertension | 160-179 | 100-109 |
| Stage 3 hypertension (hypertensive emergency) | ≥180 | ≥110 |
| Isolated systolic hypertension | ≥140 | <90 |

In some instances, lower thresholds for classification of hypertension may be used (135 mmHg systolic or 85 mmHg diastolic), e.g. if measurements are derived from 24-hour ambulatory or home monitoring.

Treatment of hypertension is to be understood herein as a reduction in blood pressure considered clinically relevant by the skilled person. Clinical trials demonstrate that lowering blood pressure can substantially reduce cardiovascular risk, and current clinical practice guidelines identify lowering blood pressure as a priority in the treatment of people with hypertension.

Preferably, the treatment described herein results in a decrease in the systolic blood pressure and/or a decrease in the diastolic blood pressure.

In one embodiment, the subject treated according to the methods of the present disclosure is a pre-hypertensive subject having a systolic blood pressure in the range of 120-139 mmHg and a diastolic blood pressure in the range of 80-89 mmHg.

In one embodiment, the subject has a systolic blood pressure above 135 mmHg and/or a diastolic blood pressure above 85 mmHg.

In one embodiment, the subject has a systolic blood pressure above 140 mmHg and/or a diastolic blood pressure above 90 mmHg.

In one embodiment, the subject suffers from stage 1 hypertension, i.e. said subject has a systolic blood pressure in the range of 140-159 mmHg and a diastolic blood pressure in the range of 90-99 mmHg.

In one embodiment, the subject suffers from stage 2 hypertension, i.e. said subject has a systolic blood pressure in the range of 160-179 mmHg and a diastolic blood pressure in the range of 100-109 mmHg.

In one embodiment, the subject suffers from stage 3 hypertension, i.e. said subject has a systolic blood pressure at or above 180 mmHg and a diastolic blood pressure at or above 110 mmHg.

In one embodiment, the subject suffers from isolated systolic hypertension, i.e. said subject has a systolic blood pressure at or above 140 mmHg and a diastolic blood pressure below 90 mmHg.

In children and adolescents (<18 years), hypertension is defined as elevated blood pressure over several visits (The Fourth Report on the Diagnosis, Evaluation, and Treatment of High Blood Pressure in Children and Adolescents; Pediatrics, August 2004, VOLUME 114/ISSUE Supplement 2). The definition of hypertension in children and adolescents is based on the normative distribution of blood pressure (BP) in healthy children. Normal BP is defined as systolic blood pressure (SBP) and diastolic blood pressure (DBP) that are <90th percentile for gender, age, and height. Hypertension is defined as average SBP or DBP that is 95th percentile for gender, age, and height on at least 3 separate occasions. Average SBP or DBP levels that are ≥90th percentile but <95th percentile had been designated as "high normal" and were considered to be an indication of heightened risk for developing hypertension. It is now recommended that, as with adults, children and adolescents with BP levels ≥120/80 mm Hg but <95th percentile should be considered prehypertensive.

In one embodiment the subject is below 18 years of age. Children with hypertension may suffer from one or more of diabetes, pre-diabetes, obesity, overeating or Prader Willi syndrome.

In one embodiment, the treatment results in a decrease in the systolic blood pressure by at least 5 mm Hg, for example at least 6 mm Hg, such as at least 7 mm Hg, for example at least 8 mm Hg, such as at least 9 mm Hg, for example at least 10 mm Hg, such as at least 12 mm Hg, for example at least 15 mm Hg, such as at least 17 mm Hg, for example at least 20 mm Hg, such as at least 22 mm Hg, for example at least 25 mm Hg, such as at least 27 mm Hg, for example at least 30 mm Hg.

In one embodiment, the treatment results in a decrease in the systolic blood pressure by at least 10 mm Hg.

In one embodiment the treatment results in a decrease in the systolic blood pressure by at least 5%, such as at least 7%, for example at least 10%, such as at least 12%, for example at least 15%, such as at least 17%, for example at least 20%, such as at least 22%, for example at least 25%.

In one embodiment, the treatment results in a decrease in the diastolic blood pressure by at least 5 mm Hg, for example at least 6 mm Hg, such as at least 7 mm Hg, for example at least 8 mm Hg, such as at least 9 mm Hg, for example at least 10 mm Hg, such as at least 12 mm Hg, for example at least 15 mm Hg, such as at least 17 mm Hg, for example at least 20 mm Hg, such as at least 22 mm Hg, for example at least 25 mm Hg, such as at least 27 mm Hg, for example at least 30 mm Hg.

In one embodiment, the treatment results in a decrease in the diastolic blood pressure by at least 10 mm Hg.

In one embodiment, the treatment results in a decrease in the diastolic blood pressure by at least 5%, such as at least 7%, for example at least 10%, such as at least 12%, for example at least 15%, such as at least 17%, for example at least 20%, such as at least 22%, for example at least 25%.

Control of hypertension is a particular focus area in obese subjects, since subjects suffering from obesity often also suffer from hypertension. The present treatment allows for concurrent treatment of hypertension and obesity. Obesity is defined herein as a medical condition in which excess body fat has accumulated to the extent that it may have an adverse effect on health, leading to reduced life expectancy and/or increased health problems in general. Thus, in one embodiment the subject is obese.

Body mass index (BMI) is a measure which compares weight and height. People are generally considered overweight or pre-obese if the BMI is between 25 and 30 and obese if the BMI is over 30. Morbidly obese subjects have a BMI over 35.

In one embodiment the subject has a BMI above 25 kg/m$^2$, such as above 30 kg/m$^2$, for example above 35 kg/m$^2$, such as above 40 kg/m$^2$.

In one embodiment the subject has a BMI above 30 kg/m$^2$.

In one embodiment the subject has a BMI above 35 kg/m$^2$.

Most people with diabetes develop high blood pressure during their life. Hypertension substantially increases the risk of diabetic complications. Diabetic complications include but are not limited to macrovascular and microvascular complications, including stroke, coronary artery disease, and peripheral vascular disease, retinopathy, nephropathy, and possibly neuropathy. Hypertension may also lead to worsening of diabetic complications. Thus, control or alleviation of hypertension is often an important aspect in the treatment of diabetic subjects.

In one embodiment, the tesofensine-metoprolol treatment described herein leads to an alleviation or improvement of diabetic complications.

In one embodiment, the subject is suffering from diabetes, such as type 1 diabetes, type 2 diabetes, pre-diabetes and gestational diabetes.

In one embodiment, the subject is suffering from type 1 diabetes.

In one embodiment, the subject is suffering from type 2 diabetes.

In one embodiment, the subject is suffering from pre-diabetes.

In one embodiment, the subject is suffering from gestational diabetes.

Type 1 diabetes (diabetes mellitus type 1) is a form of diabetes that results from the autoimmune destruction of the insulin-producing beta cells in the pancreas. In type 1 diabetes, hypertension may reflect the onset of diabetic nephropathy.

Type 2 diabetes is a metabolic disorder that is characterized by hyperglycemia in the context of insulin resistance and a relative lack of insulin. Type 2 diabetes makes up about 90% of cases of diabetes, with the other 10% due primarily to diabetes mellitus type 1 and gestational diabetes. Obesity is thought to be the primary cause of type 2 diabetes in people who are genetically predisposed to the disease. In type 2 diabetes, hypertension is often present as part of the metabolic syndrome of insulin resistance also including central obesity and dyslipidemia.

Pre-diabetes is used interchangeably herein with intermediate hyperglycaemia. Intermediate hyperglycaemia is a biochemical state in which a person has glucose levels above the normal range, but does not yet meet the criteria for a diagnosis of diabetes. The primary aim of management of intermediate hyperglycaemia is to prevent progression to diabetes.

A pre-diabetic subject may have one or more of impaired fasting glycaemia (IFG) and/or impaired glucose tolerance (IGT) and/or elevated glycated haemoglobin ($HbA_{1c}$) levels.

Weight loss can prevent progression of pre-diabetes into diabetes and can also markedly improve clinical symptoms of type 2 diabetes. Thus, weight loss is an attractive treatment strategy for pre-diabetic subjects and subjects suffering from type 2 diabetes.

In one embodiment the subject is an obese, pre-diabetic human. In one embodiment the subject is an obese subject suffering from type 2 diabetes.

Gestational diabetes is a condition in which women without previously diagnosed diabetes exhibit high blood glucose levels during pregnancy (especially during their third trimester). Gestational diabetes is caused when insulin receptors do not function properly.

The WHO diabetes diagnostic criteria are shown in the table below.

| Condition | 2 hour glucose* mmol/l (mg/dl) | Fasting glucose mmol/l (mg/dl) | $HbA_{1c}$ mmol/mol (DCCT %) |
|---|---|---|---|
| Normal | <7.8 (<140) | <6.1 (<110) | <42 (<6.0) |
| Impaired fasting glycaemia | <7.8 (<140) | ≥6.1 (≥110) & <7.0 (<126) | 42-46 (6.0-6.4) |
| Impaired glucose tolerance | ≥7.8 (≥140) | <7.0 (<126) | 42-46 (6.0-6.4) |
| Diabetes mellitus | ≥11.1 (≥200) | ≥7.0 (≥126) | ≥48 (≥6.5) |

*Venous plasma glucose 2 hours after ingestion of 75 g oral glucose load

The subject benefitting from co-treatment of tesofensine and metoprolol according to the methods of the present invention may also be a subject suffering from an obesity-associated disorder or condition, such as one selected from the group consisting of metabolic syndrome, dyslipidemia, atherosclerosis, drug-induced obesity, overeating disorders, bulimia nervosa, binge eating disorder, compulsive overeating, impaired appetite regulation, Prader-Willi Syndrome, nonalcoholic fatty liver disease (NAFLD) and nonalcoholic steatohepatitis (NASH).

In one embodiment the subject is suffering from metabolic syndrome.

In one embodiment, the subject is suffering from Prader Willi syndrome. Prader-Willi syndrome (PWS) is a genetic disorder due to loss of function of specific genes on chromosome 15. In newborns symptoms include weak muscles, poor feeding, and slow development. In childhood the person becomes constantly hungry which often leads to obesity and type 2 diabetes.

In one embodiment the subject is suffering from a fatty liver disease selected from nonalcoholic fatty liver disease (NAFLD) and nonalcoholic steatohepatitis (NASH).

Nonalcoholic fatty liver disease (NAFLD) is a cause of a fatty liver, occurring when fat is deposited in the liver (steatosis) due to other causes than excessive alcohol use. NAFLD is the most common liver disorder in Western industrialized nations. NAFLD is associated with insulin resistance and metabolic syndrome (obesity, combined hyperlipidemia, diabetes mellitus (type II) and high blood pressure). Non-alcoholic steatohepatitis (NASH) is the most extreme form of NAFLD, and is a major cause of cirrhosis of the liver. NASH is a state in which the steatosis is combined with inflammation and fibrosis (steatohepatitis).

In one embodiment, the obesity-associated disorder or condition is nonalcoholic fatty liver disease (NAFLD).

In one embodiment, the obesity-associated disorder or condition is nonalcoholic steatohepatitis (NASH).

In one embodiment, the present disclosure relates to a method for co-treatment of hypertension and obesity in a subject in need thereof, the method comprising administering to said subject:
  i) a therapeutically effective amount of tesofensine or a pharmaceutically acceptable salt thereof; and
  ii) a therapeutically effective amount of metoprolol or a pharmaceutically acceptable salt thereof,
thereby reducing blood pressure and body weight of said subject.

Co-administration of tesofensine and metoprolol is capable of preventing cardiovascular side-effects of tesofensine, i.e. prevent increases in heart rate and blood pressure induced by tesofensine. Thus, in one embodiment, the present disclosure further relates to prevention or alleviation of cardiovascular side-effects of tesofensine.

In one embodiment, the present disclosure relates to a method for reduction of weight and blood pressure in a subject in need thereof, the method comprising administering to said subject:
  i) a therapeutically effective amount of tesofensine or a pharmaceutically acceptable salt thereof; and
  ii) a therapeutically effective amount of metoprolol or a pharmaceutically acceptable salt thereof,
thereby reducing blood pressure and weight of said subject.

In one embodiment, the present disclosure relates to a method for co-treatment of hypertension and diabetes (in particular type 2 diabetes) in a subject in need thereof, the method comprising administering to said subject:
  i) a therapeutically effective amount of tesofensine or a pharmaceutically acceptable salt thereof; and
  ii) a therapeutically effective amount of metoprolol or a pharmaceutically acceptable salt thereof, thereby reducing blood pressure and treating diabetes of said subject.

In one embodiment, the present disclosure relates to a method for co-treatment of hypertension and an obesity related disorder as herein defined in a subject in need thereof, the method comprising administering to said subject:
i) a therapeutically effective amount of tesofensine or a pharmaceutically acceptable salt thereof; and
ii) a therapeutically effective amount of metoprolol or a pharmaceutically acceptable salt thereof,
thereby reducing blood pressure and treating the obesity related disorder of said subject.

In one embodiment, the present disclosure relates to a method for co-treatment of hypertension and a fatty liver disease, such as NAFLD or NASH, in a subject in need thereof, the method comprising administering to said subject:
i) a therapeutically effective amount of tesofensine or a pharmaceutically acceptable salt thereof; and
ii) a therapeutically effective amount of metoprolol or a pharmaceutically acceptable salt thereof,
thereby reducing blood pressure and treating the fatty liver disease of said subject.

In one embodiment the present disclosure relates to a method for treatment of hypertension, obesity and diabetes in a subject in need thereof, the method comprising administering to said subject:
i) a therapeutically effective amount of tesofensine or a pharmaceutically acceptable salt thereof; and
ii) a therapeutically effective amount of metoprolol or a pharmaceutically acceptable salt thereof.

In one embodiment the present disclosure relates to a method for treating, alleviating or preventing diabetic complications in a subject in need thereof, the method comprising administering to said subject:
i) a therapeutically effective amount of tesofensine or a pharmaceutically acceptable salt thereof; and
ii) a therapeutically effective amount of metoprolol or a pharmaceutically acceptable salt thereof.

In one embodiment, the present disclosure relates to a composition comprising tesofensine or a pharmaceutically acceptable salt thereof and metoprolol or a pharmaceutically acceptable salt thereof, for use in the treatment of hypertension.

In one embodiment, the present disclosure relates to a composition comprising tesofensine or a pharmaceutically acceptable salt thereof and metoprolol or a pharmaceutically acceptable salt thereof, for use in the treatment of hypertension and obesity.

In one embodiment, the present disclosure relates to a composition comprising tesofensine or a pharmaceutically acceptable salt thereof and metoprolol or a pharmaceutically acceptable salt thereof, for use in the treatment of hypertension and diabetes.

In one embodiment, the present disclosure relates to a composition comprising tesofensine or a pharmaceutically acceptable salt thereof and metoprolol or a pharmaceutically acceptable salt thereof, for use in the treatment of hypertension and a fatty liver disorder.

In one embodiment, the present disclosure relates to a composition comprising tesofensine or a pharmaceutically acceptable salt thereof and metoprolol or a pharmaceutically acceptable salt thereof, for use in the treatment of hypertension and an obesity related disorder as herein defined.

In one embodiment, the present disclosure relates to a composition comprising tesofensine or a pharmaceutically acceptable salt thereof and metoprolol or a pharmaceutically acceptable salt thereof, for use in the treatment of hypertension, obesity and diabetes.

In one embodiment, the present disclosure relates to a composition comprising tesofensine or a pharmaceutically acceptable salt thereof and metoprolol or a pharmaceutically acceptable salt thereof, for use in treating, alleviating or preventing diabetic complications.

In one embodiment, the present disclosure relates to the use of a composition comprising tesofensine or a pharmaceutically acceptable salt thereof and metoprolol or a pharmaceutically acceptable salt thereof, for the manufacture of a medicament for the treatment of hypertension, optionally further for the treatment of obesity and/or diabetes.

The tesofensine and metoprolol according to the present disclosure may be administered simultaneously, sequentially or separately.

In one embodiment, the tesofensine and the metoprolol are co-administered as a single composition. In such compositions, at least part of the metoprolol may advantageously be formulated to exhibit an extended release profile. In one embodiment, the composition comprising tesofensine and metoprolol is as described in WO 2016/138908 (claiming priority from PA 2015 70117 and PA 2015 70644), which are incorporated by reference in their entirety.

An example of a single composition comprising both tesofensine and metoprolol is a pharmaceutical composition comprising
a. a first composition comprising an extended release (ER) composition of metoprolol or a pharmaceutically acceptable salt thereof,
b. a second composition comprising tesofensine or a pharmaceutically acceptable salt thereof, and
c. a third composition comprising an immediate release (IR) composition with metoprolol or a pharmaceutically acceptable salt thereof.

In one embodiment Tesofensine and Metoprolol are present in one dosage form with three phases in the following absolute amounts per dosage form.

| Metoprolol extended release | Metoprolol immediate release | Tesofensine immediate release |
| --- | --- | --- |
| 20-200 mg | 5-50 mg | 0.1-1.5 mg |
| 75-125 mg | 10-25 mg | 0.25-0.75 mg |
| 75-80 mg | 10-15 mg | 0.25-0.75 mg |
| 100 mg | 25 mg | 0.5 mg |
| 100 mg | 10 mg | 0.5 mg |
| 80 mg | 20 mg | 0.5 mg |
| 20 mg | 5 mg | 0.2 mg |

In one embodiment, the dosage form comprises a tri-layer dosage unit having an extended release (ER) phase layer with metoprolol, and one immediate release phase layer with metoprolol and another immediate release layer with tesofensine. The ER phase contains a therapeutically effective amount of metoprolol, suitably in granulate form.

In other embodiments, the dosage form is a bi-layer tablet having an ER phase layer with metoprolol and one immediate release layer with both metoprolol and tesofensine.

The composition comprising tesofensine and metoprolol may further comprise one or more adjuvants, excipients, carriers and/or diluents.

In some embodiments, the composition comprising tesofensine and metoprolol may comprise one or more further therapeutic and/or prophylactic agents known in the art to treat hypertension and/or obesity and/or diabetes.

The tesofensine and metoprolol may be administered by any convenient route, which suits the desired therapy. Preferred routes of administration include oral administration, in particular in tablet, in s, in drage, in powder, or in liquid form, and parenteral administration, in particular cutaneous, subcutaneous, intramuscular, or intravenous injection. Preferably, the tesofensine and metoprolol are administered orally.

Compositions comprising tesofensine and metoprolol as described herein may be manufactured by the skilled person by use of standard methods and conventional techniques appropriate to the desired formulation. When desired, compositions adapted to give sustained release of the active ingredient may be employed.

Further details on techniques for formulation and administration may be found in the latest edition of Remington's Pharmaceutical Sciences (Maack Publishing Co., Easton, PA).

The subject treated is preferably a human, such as an adult human aged 18 or older. In other embodiments the subject is a child or an adolescent below 18 years of age.

The data in the present application shows that co-administration of tesofensine and metoprolol unexpectedly result in a significant decrease in both systolic and diastolic blood pressure. The effect on blood pressure in response to co-administration of tesofensine and metoprolol is greater than has been shown by metoprolol alone (Kostis et al (Circulation 75(1), 204-212, 1987).

Thus, in one embodiment, the present disclosure relates to a method for improving the therapeutic effect of metoprolol, particularly for improving the effect of metoprolol on blood pressure, the method comprising co-administration of metoprolol and tesofensine as described herein to a subject in need thereof.

EXAMPLES

Example 1. Effect of Tesofensine on Metoprolol Pharmacokinetics

The ability of tesofensine to inhibit CYP2D6 in the clinical setting was investigated in a Phase 1 drug-drug interaction (DDI) study with metoprolol, which is a known substrate for CYP2D6.

Subjects

Healthy human male volunteers, 18-50 years of age. A total of 14 subjects were included in the study.

Methodology

Two consecutive study periods separated by a washout period of at least three days. The sequence of events was the same for all subjects. In period 1, a single dose of metoprolol was administered. In period 2, the same dose of metoprolol was administered at a steady state concentration of tesofensine.

Metoprolol: 50 mg single dose

Tesofensine: 2 mg loading dose at days 1-3, 0.5 mg maintenance dose at days 4-14

Results

The single dose metoprolol pharmacokinetics (PK) obtained at day 0 was compared to the PK obtained after 14 days of tesofensine once daily administration.

The results are depicted in FIG. 1. The results show that tesofensine caused a small (15%), but statistically significant increase in metoprolol AUC with no effect on either Tmax or Cmax. The results indicate that tesofensine is capable of increasing the bioavailability of metoprolol through its inhibitory action on CYP2D6.

Example 2. Effect of Tesofensine and Metoprolol on Heart Rate and Blood Pressure in Humans In a retrospective analysis of the data obtained in the above-mentioned Phase 1 DDI study the effect of a single dose of metoprolol in subjects treated with tesofensine was investigated. Particularly, the effect of tesofensine-metoprolol on heart rate and blood pressure at rest, was investigated.

Figure 2:
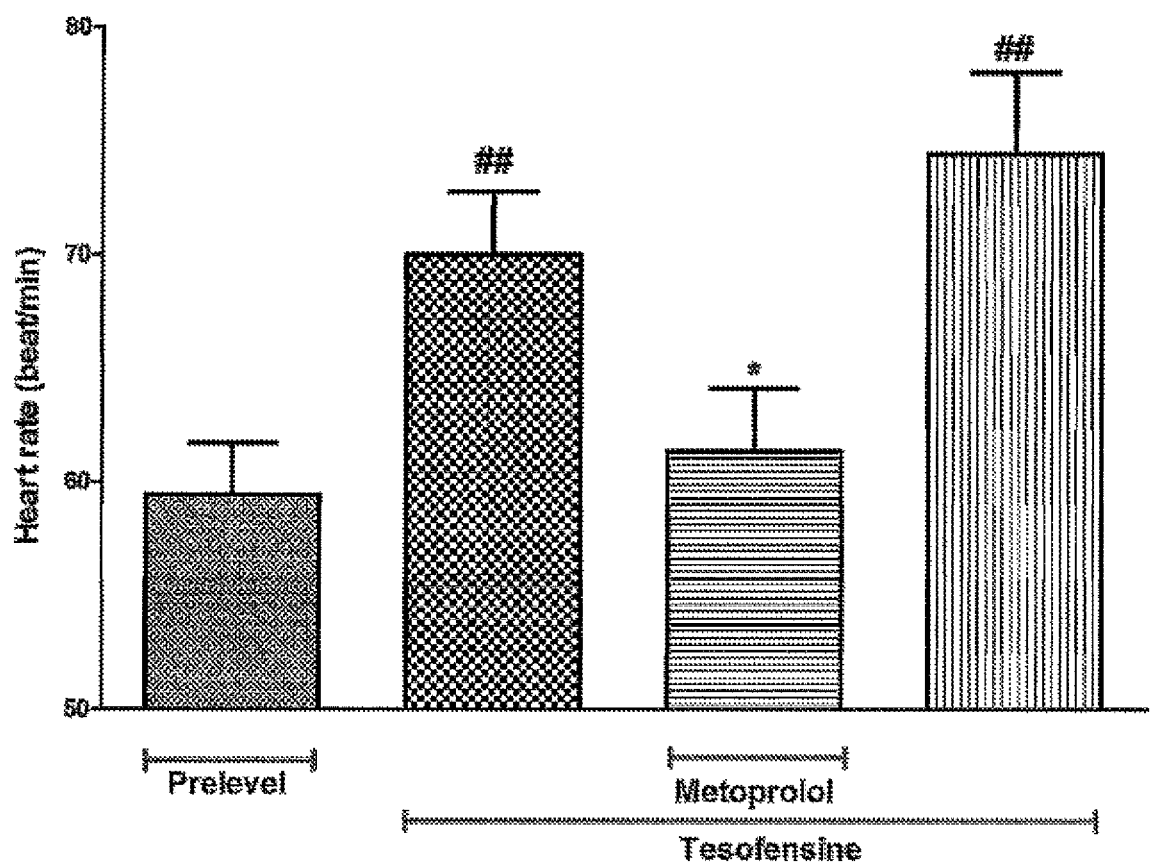
FIG. 2. Increase in heart rate (HR) caused by 14 days tesofensine dosing is suppressed by a single metoprolol administration. Column 1: prelevel HR; column 2: HR after 14 days of tesofensine; column 3: HR measured on day 14, 7 hours after a single metoprolol dose in tesofensine treated subjects; column 4: HR measured on day 15, 24 hours after a single metoprolol dose in tesofensine treated subjects. *p<0.05 vs tesofensine, ##p<0.01 vs prelevel. By 't' test—Wilcoxon matched-pairs signed rank test.

Metoprolol was found to normalize the tesofensine-induced increase in heart rate after 7 hours (FIG. 2, $3^{rd}$ column) as previously shown pre-clinically. In accordance with the pharmacokinetics of metoprolol (plasma T ½ 3-4 hours)—the effect on the heart rate disappeared after ~24 hours (FIG. 2, 4th column). The data indicates that co-administration of tesofensine and metoprolol is capable of inhibiting the tesofensine-induced increase in heart rate in human subjects to levels approximating pre-treatment levels.

Figure 3:
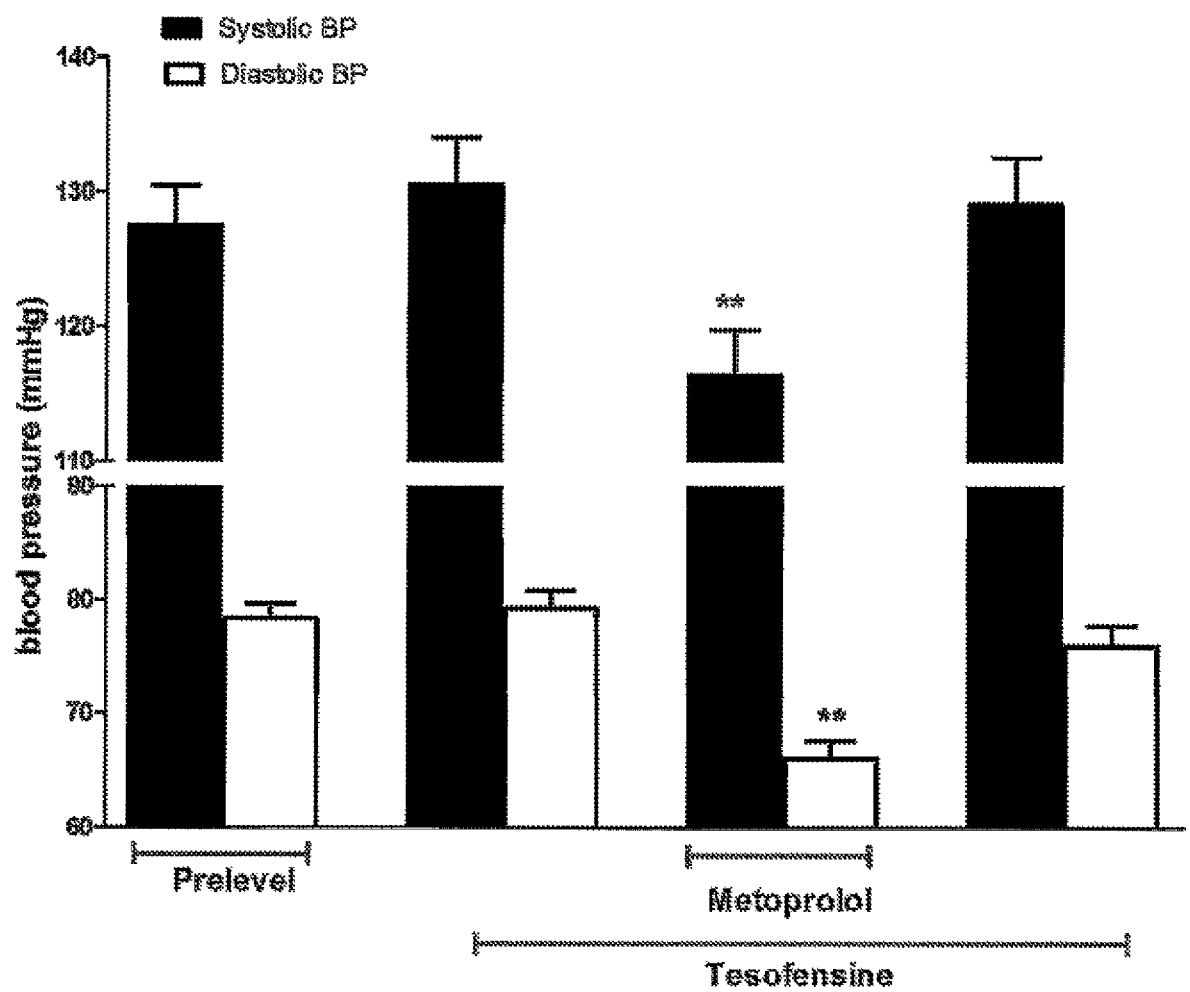
FIG. 3. Systolic and diastolic blood pressure after 14 days tesofensine dosing followed by a single metoprolol administration. A single metoprolol administration reduced both systolic and diastolic blood pressure (BP) in tesofensine treated subjects to levels below pretreatment levels. Column 1: prelevel BP; column 2: BP after 14 days of tesofensine; column 3: BP measured on day 14, 7 hours after a single metoprolol dose in tesofensine treated subjects; column 4: BP measured on day 15, 24 hours after a single metoprolol dose in tesofensine treated subjects. **P<0.01 vs tesofensine (Wilcoxin matched-pairs signed rank test, n=14).

In the present study, 14 days of tesofensine treatment was found to increase systolic BP slightly, while diastolic BP was essentially not altered by tesofensine treatment (FIG. 3, column 2). The slight increase in systolic BP in response to tesofensine treatment was not significant. However, statistically significant decreases in the systolic and diastolic blood pressures were observed after metoprolol administration at day 14 (FIG. 3, column 3) as compared to pre-treatment levels and also compared to subjects treated with tesofensine only. Systolic BP in response to tesofensine-metoprolol co-administration was found to be decreased by about 11 mm Hg as compared to pre-treatment levels and by about 14 mm Hg as compared to subjects treated with tesofensine only. Diastolic BP in response to tesofensine-metoprolol co-administration was found to be decreased by about 12 mm Hg as compared to pre-treatment levels and by about 13 mm Hg as compared to subjects treated with tesofensine only. This corresponds to a decrease in systolic BP by more than 8% and a decrease in diastolic BP by more than 15% as compared to pre-treatment levels.

The data presented herein indicates that co-administration of tesofensine and metoprolol significantly reduce both systolic and diastolic BP to a larger degree than metoprolol treatment alone (Kostis et al (Circulation 75(1), 204-212, 1987). Thus, the data herein indicates that tesofensine and metoprolol co-administration is an attractive treatment strategy for hypertensive subjects. In particular for treatment of obese hypertensive subjects as such subjects would benefit greatly from both the weight-reducing effect of tesofensine and the BP-lowering effect of tesofensine and metoprolol.

As shown herein, tesofensine may increase bioavailability of metoprolol slightly through its inhibitory effect on CYP2D6 (Example 1). However, it is unlikely that the significant decrease in blood pressure described herein in human subjects in response to tesofensine-metoprolol co-administration can be explained solely by this action. Additionally, the blood pressure lowering effect of tesofensine-metoprolol co-administration was highly surprising in view of animal studies showing that co-administration of tesofensine and metoprolol merely prevented tesofensine-induced increases in heart rate and blood pressure (WO 2013/120935 and Hjorth Bentzen et al 2013; Obesity; Vol 21(5), p. 985-992).

Example 3 Phase 2a Trial Entitled "a Double-Blind, Randomized, Placebo-Controlled, Multiple-Dose, Two-Center Safety, and Efficacy Study of Co-Administration of Tesofensin/Metoprolol (Tesomet) in Subjects with Type 2 Diabetes Mellitus (NCT02737891)

The trial comprised a total of 60 patients with a mean BMI of 32.59 randomized into two groups of each 30 patients:

Arm 1 were administered tesofensine 0.5 mg (tablets)+ metoprolol 100 mg (MetoHEXAL® 100 mg retard tablets) once a day (Tesomet); Arm 2 were administered Placebo matching tablets once a day. Patients were treated for 90 days. The patients at enrolment had an average BMI of 32.59.

Inclusion Criteria:
1. Males and females
2. Confirmed diagnosis of T2DM
3. 18-70 years of age
4. HbA1c≥7.0%

Exclusion Criteria:
1. Hypersensitivity to tesofensine/metoprolol
2. Heart failure class II or greater according to the New York Heart Association (NYHA) or decompensated heart failure
3. History of myocardial infarction or stroke within 12 months prior to enrolment
4. History of coronary revascularisation or angioplasty in the last 12 months prior to enrolment
5. Patients reporting angina in the last 6 months prior to enrolment
6. Treatment with insulin and/or other injectable antidiabetic medications, or TZDs
7. Any clinically significant cardiac arrhythmia Results 58 patients completed the study. The study demonstrated a statistically significant reduction in bodyweight during the course of the study (day 0 to day 90) of 3.50 kg (3.54%) in the treatment group compared to a reduction of 0.29 kg (0.31%) in the placebo group (p<0.0001). The reduction in body weight correlated with a decrease in waist circumference of 2.29 cm in the Tesomet treatment group compared to a reduction of 0.03 cm for patients receiving placebo (p<0.007).

Both systolic and diastolic blood pressures were numerically reduced in the treatment group from baseline at day 0 to day 90. Systolic blood pressure was numerically reduced by an average of 3.10 mmHg for patients treated with Tesomet compared to an average decrease of 0.66 mmHg for patients dosed with placebo. Diastolic blood pressure was numerically reduced by an average of 2.21 mmHg for patients treated with Tesomet compared to an average decrease of 0.19 mmHg for patients dosed with placebo.

The invention claimed is:

1. A method for treating hyperphagia in a subject having Prader Willi Syndrome comprising orally administering to the subject
   0.1 mg to 1 mg of tesofensine or a pharmaceutically acceptable salt thereof; and
   10 mg to 200 mg of metoprolol or a pharmaceutically acceptable salt thereof.

2. The method according to claim 1, wherein the tesofensine or a pharmaceutically acceptable salt thereof and the metoprolol or a pharmaceutically acceptable salt thereof are administered simultaneously, sequentially or separately.

3. The method according to claim 1, wherein the tesofensine or a pharmaceutically acceptable salt thereof and the metoprolol or a pharmaceutically acceptable salt thereof are co-administered as a single pharmaceutical composition.

4. The method according to claim 3, wherein the single pharmaceutical composition comprises
   a first composition comprising an extended release (ER) composition of metoprolol or a pharmaceutically acceptable salt thereof,
   a second composition comprising tesofensine or a pharmaceutically acceptable salt thereof, and
   a third composition comprising an immediate release (IR) composition with metoprolol or a pharmaceutically acceptable salt thereof.

5. The method according to claim 3, wherein the single pharmaceutical composition is in the form of a capsule.

6. The method according to claim 1, wherein the tesofensine or a pharmaceutically acceptable salt thereof is administered to said subject at a dose of 0.25 mg to 0.75 mg of tesofensine per day.

7. The method according to claim 1, wherein the metoprolol or a pharmaceutically acceptable salt thereof is administered to said subject at a dose of 25 mg to 100 mg of metoprolol per day.

8. The method according to claim 1, wherein the subject is an adult human.

9. The method according to claim 8, wherein the subject has a body mass index (BMI) of 25 kg/m$^2$ or a BMI of above 25 kg/m$^2$, prior to the administration.

10. The method according to claim 8, wherein the administration results in reduction of the subject's BMI, as compared to prior to the administration.

11. The method according to claim 1, wherein the subject is below 18 years of age.

12. The method according to claim 11, wherein the administration results in decrease of the subject's waist circumference, as compared to prior to the administration.

* * * * *